(12) United States Patent
Rioux et al.

(10) Patent No.: US 7,828,744 B2
(45) Date of Patent: Nov. 9, 2010

(54) METHOD AND ASSEMBLY FOR BREAST IMMOBILIZATION

(75) Inventors: Robert Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 784 days.

(21) Appl. No.: 10/422,409

(22) Filed: Apr. 23, 2003

(65) Prior Publication Data

US 2004/0215101 A1    Oct. 28, 2004

(51) Int. Cl.
*A61B 10/00* (2006.01)
(52) U.S. Cl. ..................................... 600/562
(58) Field of Classification Search ............... 606/167, 606/170, 130; 604/22, 74; 600/562, 564–567
See application file for complete search history.

(56) References Cited

U.S. PATENT DOCUMENTS

| | | | | |
|---|---|---|---|---|
| 1,808,216 | A * | 6/1931 | Friedman ................ 292/307 R |
| 3,375,726 | A * | 4/1968 | Jones et al. ................. 474/241 |
| 4,580,561 | A * | 4/1986 | Williamson ................. 606/130 |
| 5,176,623 | A * | 1/1993 | Stetman et al. ............... 602/27 |
| 5,534,778 | A * | 7/1996 | Loos et al. ................... 324/318 |
| 5,571,084 | A | 11/1996 | Palmer |
| 5,702,405 | A * | 12/1997 | Heywang-Koebrunner .. 606/130 |
| 5,706,812 | A * | 1/1998 | Strenk et al. ................. 600/417 |
| 5,833,627 | A * | 11/1998 | Shmulewitz et al. ........ 600/562 |
| 5,913,863 | A * | 6/1999 | Fischer et al. ................ 606/130 |
| 6,050,954 | A * | 4/2000 | Mittermeier ................ 600/562 |
| 6,146,377 | A * | 11/2000 | Lee et al. ....................... 606/13 |
| 6,203,499 | B1 * | 3/2001 | Imling et al. ................. 600/461 |
| 6,287,521 | B1 * | 9/2001 | Quay et al. ................... 422/101 |
| 6,304,770 | B1 * | 10/2001 | Lee et al. ..................... 600/427 |
| 6,440,100 | B1 | 8/2002 | Prentiss |
| 6,569,176 | B2 * | 5/2003 | Jesseph ....................... 606/167 |
| 6,577,702 | B1 * | 6/2003 | Lebovic et al. ................ 378/37 |
| 6,589,254 | B2 * | 7/2003 | Fontenot ...................... 606/130 |
| 6,676,610 | B2 * | 1/2004 | Morton et al. ............... 600/573 |
| 2002/0026126 | A1 * | 2/2002 | Burdorff et al. ............. 600/564 |
| 2003/0130575 | A1 * | 7/2003 | Desai ........................... 600/417 |

FOREIGN PATENT DOCUMENTS

EP    0 995 399    4/2000
WO    WO 02/38032    5/2002

OTHER PUBLICATIONS

PCT Partial International Search for PCT/US2004/010590, Applicant: Scimed Life Systems, Inc., Forms PCT/ISA/206, dated Aug. 26, 2004 (5 pages).

* cited by examiner

*Primary Examiner*—Max Hindenburg
*Assistant Examiner*—Fangemonique Smith
(74) *Attorney, Agent, or Firm*—Vista IP Law Group LLP

(57) ABSTRACT

A device, method, and system are provided for immobilizing and stabilizing a breast in preparation for tumor ablation or biopsy while the patient is lying supine. The breast is lifted away from the chest wall of the patient, so that the tissue abnormality to be treated is also lifted away from the chest wall. This reduces the possibility of damage to the neighboring costochondral wall and the surrounding healthy tissue. The device includes a medical device holder that can be used to accurately aim a medical probe, and hold it in place during treating.

18 Claims, 12 Drawing Sheets

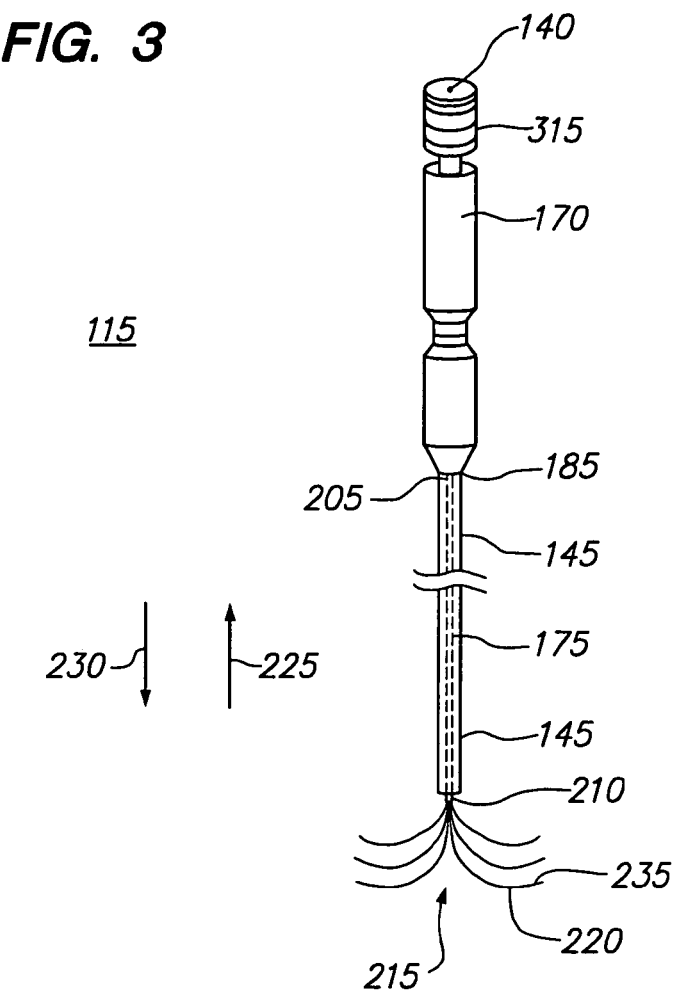
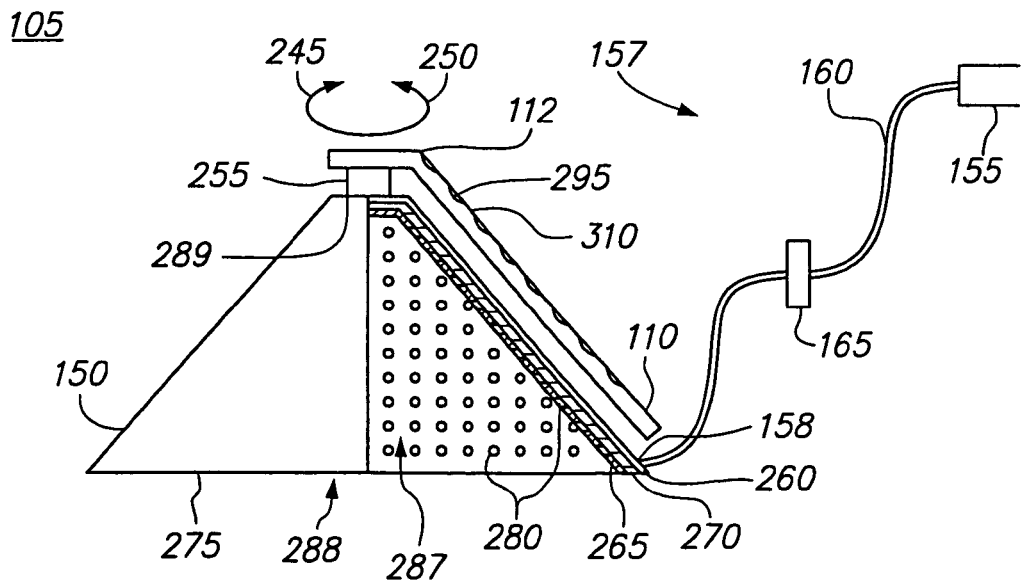

610

505

METHOD AND ASSEMBLY FOR BREAST IMMOBILIZATION

FIELD OF THE INVENTION

The field of the present invention relates to the medical treatment of breast tissue, and more particularly to breast immobilization in preparation for the treatment.

BACKGROUND OF THE INVENTION

Radio frequency (RF) energy can be used to ablate solid tissue, thus inducing localized tissue necrosis. RF energy is particularly useful in this capacity for inducing necrosis in sub-dermal lesions and tumors such as those found in cancers of the liver, stomach, kidney, lung, bowel, pancreas, and breast. The conventional delivery system for this sort of treatment is an electro-surgical probe, and one benefit to using such a probe is that it is much less invasive than a full surgical procedure to remove the pathology. As a consequence, recovery time, morbidity, and mortality are greatly reduced, and costs are lowered.

As radio frequency thermal ablation (RFA) technology has been refined, it has become possible to ablate relatively large tumors using image guided probe placement. The imaging techniques available include computerized axial tomography scanning, magnetic resonance imaging, ultrasound imaging, and laparoscopy.

As RFA and other minimally invasive treatments of localized cancers evolve, support equipment is needed to increase the efficiency and efficacy of the treatment. This is particularly true in the use of RFA for treating breast disorders because of the pliability of the tissue involved. This tissue pliability also complicates the taking of a percutaneous biopsy of a suspected abnormality—an important step in diagnosing breast cancer.

The difficulty arises because when a patient lies supine—i.e., on her (or his) back—the breasts fall back as a result of natural gravitational effects, and are compressed onto the costochondral wall, i.e. onto the rib cage. In the process, the tissue abnormality also falls back and settles closer to the rib cage than when the patient is upright. This natural repositioning of the breast presents at least three significant treatment problems.

First, since the abnormality is in a different location than it was when the patient was upright, it is difficult, without ongoing imaging assistance, to accurately aim the medical instrument—either an ablation probe or a biopsy needle—so that upon insertion it goes directly into the abnormality. This problem is exacerbated by the fact that as the medical instrument is inserted into the tissue, the breast tissue naturally shifts because of the force of insertion due to the breast's pliability. This in turn causes the abnormality to move around during treatment.

Second, and perhaps more significantly, since the abnormality is now closer to the rib cage, there is a serious risk that treatment will damage the neighboring costochondral wall and the surrounding healthy tissue. In addition, since the breast is compressed due to gravity, the abnormality may also be closer to the skin surface. Therefore, the ablation process has the potential to cause dermal blistering.

Third, as alluded to above, it is useful to apply an imaging technique during treatment, while the patient is lying supine. This enables the physician to monitor the progress of the treatment, and thus make suitable adjustments to avoid damaging healthy tissue on the one hand, and to ablate all of the cancerous tissue on the other hand. Imaging techniques typically make use of the fact that tumor tissue is denser than healthy tissue, and the images show this density differential as a visual contrast. However, when the breast is compressed while the patient is lying supine, the healthy tissue has the appearance of being denser than normal, while the cancerous tissue's density remains essentially unchanged. Therefore, the effectiveness of the imaging process in identifying the tumor is compromised, or at the very least reduced, since the sharpness of the visual contrast is decreased.

One approach to obviating these problems is to use a stereotactic table. A stereotactic table is a table—mounted on a hydraulic lift—that has a hole in it. In use, the patient lies prone on the table, with a breast suspended through the hole, and the physician works on the breast underneath the table. The stereotactic table certainly addresses the problems associated with breast compression due to gravity, since gravity is now used to pull the breast away from the chest wall. However, the table has some serious drawbacks that make it a less than optimal solution to the problems described above.

As of December 2002, each table costs approximately $250,000 US. As a consequence of this high price, there are only about 1,500 units in use in the entire United States. In addition, the table is often uncomfortable for the patient who has to lie prone, with the head cocked to the side, sometimes for up to 45 minutes.

There are devices available that are used for immobilizing or stabilizing other tissue in the body in preparation for tissue ablation or biopsy. However, none of these devices is specific to the breast, and they are, in fact, generally unsuitable for breast immobilization. Indeed, most are designed for use in coronary artery bypass surgery.

For example, temporary immobilization of a local area of tissue has become common in coronary artery bypass surgery, to eliminate cardiac arrest and the need for cardiopulmonary bypass during the bypass surgery. In *Placement Of Coronary Artery Bypass Graft Without Pump Oxygenator,* 19 Annals Thorac. Surg., No. 1, at 1-9 (January 1975), Trapp and Bisarya describe immobilizing the area of the bypass graft by encircling sutures deep enough to incorporate enough muscle to suspend an area of the heart and prevent damage to the coronary artery. More recently, Fanning, et al., in *Reoperative Coronary Artery Bypass Grafting Without Cardiopulmonary Bypass,* 55 Annals Thorac. Surg., at 486-89 (February 1993), report immobilizing the area of the bypass graft with stabilization sutures.

A local cardiac immobilization surgical device is discussed in U.S. Pat. No. 5,782,746. The device is used to obtain local cardiac immobilization by temporarily attaching a rigid or semi-rigid cardiac immobilizing member to the heart. This is accomplished by utilizing a partial vacuum between the boundaries of the cardiac immobilizing member and the surface of the heart. In addition, a method and apparatus for temporarily immobilizing a local area of tissue is discussed in U.S. Pat. No. 6,364,826. The method and apparatus are used to temporarily immobilize a local area of heart tissue, so that surgery can be performed on a coronary vessel in that area without significant deterioration of the pumping function of the beating heart.

A physician working on the breast of a patient who is lying supine could, of course, simply manually hold the breast up and away from the chest wall. However, although this approach is, admittedly, much cheaper than the prohibitively expensive stereotactic table, it is decidedly unsatisfactory for a couple of reasons.

First, the physician who holds the breast in one hand only has one hand free to perform the procedure. This means that the physician has very limited access to the medical probe controls. An assistant could be called upon to hold the breast, but unless the physician and the assistant are perfectly coordinated with each other, there is the real potential for surgical error, and at the very least, unnecessary damage to healthy tissue. In addition, there is the possibility of injury to the assistant.

Second, manually holding the breast fails to provide uniform stability and immobilization, since the person holding the breast may get tired—especially if the procedure takes a long time to perform. Therefore, the medical device—either an ablating probe or a biopsy needle—may move around inside the patient in an unintended fashion, possibly causing damage to healthy tissue, or insufficiently ablating the cancerous tissue.

Thus, the available technology fails to provide a satisfactory way to immobilize and stabilize a breast so that tissue ablation, or biopsy, or any other treatment to the breast, can be effectively performed.

Consequently, there is a significant need for a device and method for immobilizing and stabilizing a breast in preparation for tumor ablation, or biopsy, or other medical treatment, that causes minimal discomfort to the patient, can be used with appropriate imaging technology so that the treatment can be monitored while it is being performed, and is inexpensive.

SUMMARY OF THE INVENTION

In accordance with a first aspect of the present invention, a breast immobilization assembly is provided. The breast immobilization assembly comprises a vacuum housing having a cavity for applying a vacuum to a breast, and a medical device holder configured to be fixed relative to the vacuum housing. The vacuum housing can be a cup, and the cup can, for example, be conically shaped. The vacuum housing can include an access opening to expose a portion of the breast when housed within the cavity. In particular, a sectional portion of the cup can be removed to form the access opening. For example, a quarter section, or a section greater than a quarter, can be removed to provide access to the breast.

By way of non-limiting example, the vacuum housing can include a vacuum conduit formed through the vacuum housing in communication with the cavity. The vacuum housing has an inner wall and an outer wall, with the vacuum conduit being formed between the inner and outer walls. The vacuum conduit has a chamber and a plurality of openings in communication between the chamber and the cavity. These openings can be holes. In one preferred embodiment, the breast immobilization assembly may further comprise a vacuum source in communication with the vacuum conduit. The vacuum source generates a sufficient vacuum so that the inner surface of the housing adheres to the surface of the breast. In addition, a relief valve in communication with the vacuum conduit can be included.

In the preferred embodiment, the medical device holder is mounted to the vacuum housing, but can also be mounted to some other stable object that is in a fixed relation with the vacuum housing. The holder can be optionally detachable, and it can be rotatably mounted to the vacuum housing. The medical device holder can be configured to hold any medical device, for example, an ablation probe or a biopsy needle. In one embodiment it comprises an arm and a plurality of holes extending lengthwise along the arm. In another embodiment it comprises an arm and a plurality of opposing fingers extending lengthwise along the arm. In addition, the medical device holder may include a locking mechanism for locking it into place so that it does not move with respect to the breast immobilizing assembly.

In accordance with a second aspect of the present invention, a medical system for use with a breast tissue is provided. The medical system comprises a vacuum housing that may have features similar to that previously described, and a medical probe, for example, an ablation probe or a biopsy needle, configured to be introduced through the access opening of the vacuum housing into the exposed portion of the breast.

The medical system may optionally include a vacuum source in communication with the vacuum housing, and a medical device holder having features similar to that previously described.

In accordance with a third aspect of the present invention, a method of performing a medical procedure on target tissue of a breast is provided. The method comprises applying a vacuum to immobilize the breast, and inserting a medical probe into the breast in contact with the target tissue. By way of non-limiting example, the application of the vacuum may advantageously move the target breast tissue away from a chest wall. The vacuum may be applied by placing the breast within a cavity of a vacuum housing, for example, a cup, and removing air from the cavity. In one preferred method, the medical probe is guided into the breast in registration with the vacuum housing. Prior to guiding the medical probe into the breast, the medical probe may be rotated relative to the vacuum housing and then fixed relative to the vacuum housing. The method may involve, for example, ablating the target tissue with the medical probe, or taking a sample of the target tissue with the medical probe. Once the probe has been used in the target tissue, it can then be removed from the breast.

In accordance with a fourth aspect of the present invention, an assembly for immobilizing a breast is provided. The breast immobilization assembly, comprises a support member configured for at least partially encompassing a base of a breast to support the breast mass, and a medical device holder configured to be fixed relative to the support member. The support member can be various shapes. For example, it can be circular, elliptic, or oval.

In one preferred embodiment the breast immobilization assembly has an expandable member disposed on an inner surface of the support member. The expandable member is configured to lift the breast when expanded. The expandable member can include an inflatable member, and a pump in communication with the inflatable member.

In an alternate preferred embodiment, the support member comprises first and second members slideably affixed to each other. These two members can be semi-circular in shape, and can be configured so that the second member is configured to slide within the first member. One of the two members can include one or more slots, and the other member can have one or more cams that slide within the one or more slots. In this preferred embodiment the first and second members are configured to lift the breast when slid towards each other. In addition, this embodiment may include a cushioning member disposed on inner surfaces of the first and second members.

In either of these preferred embodiments, a medical device holder can optionally be mounted to the support member. The medical device holder can be detachably or rotatably mounted or both, to the support member. The medical device holder can be configured for holding any medical device, such as, for example, an ablation probe or a biopsy needle. The medical device holder may have a curved member having opposing ends that are mounted to opposing sides of the support member. In one preferred embodiment, the curved member has a plurality of holes extending lengthwise along the curved member. In another preferred embodiment, the curved member has a plurality of opposing fingers extending lengthwise along the arm. The medical device holder may optionally include a locking mechanism.

In accordance with a fifth aspect of the present invention, a medical system for use with a breast is provided. The medical system comprises a support member configured for at least partially encompassing a base of the breast to support the breast mass, and a medical probe—for example, an ablation probe or biopsy needle—configured to be introduced into the breast. The support member may have features similar to those previously described. The medical system may optionally include a medical device holder having features similar to those previously described.

In accordance with a sixth aspect of the present invention, a method of performing a medical procedure on target tissue of a breast is provided. The method comprises applying a compressive force to the base of the breast in a controlled manner, and inserting a medical probe into the breast in contact with the target tissue. By way of non-limiting example, the application of the compressive force may move the target breast tissue away from the chest wall. In one preferred method, the application of the compressive force comprises constraining the base of the breast within a support member such as one of the support members previously described.

In this method, the medical probe may be guided into the breast in registration with the support member. For example, prior to guiding the medical probe into the breast, the medical probe may be rotated about the support member, and then fixed relative to the support member. In one method, the target tissue is ablated with the medical probe. In another preferred method, a sample of the target tissue is taken with a biopsy needle. Once the ablating or sampling is complete, the medical probe may be removed from the breast.

In accordance with a seventh aspect of the present invention, a medical system for use with a breast of a patient is provided. The medical system comprises a medical probe (such as, for example, an ablation probe or a biopsy needle), a breast immobilizer for immobilizing and lifting the breast away from a chest wall of the patient while the patient is lying supine, and a medical device holder for holding the medical probe relative to the breast immobilizing assembly. In one preferred embodiment, the breast immobilizer comprises a vacuum housing having a cavity for applying a vacuum to a breast, in which case, the vacuum housing may comprise an access opening to expose a portion of the breast when housed within the cavity.

In another preferred embodiment, the breast immobilizer comprises a support member configured for at least partially encompassing the base of the breast to support the breast mass. In this case, an expandable member, for example, an inflatable member, may optionally be disposed on an inner surface of the support member, and the expandable member may be configured to lift the breast when expanded. Moreover, there can be a pump in communication with the inflatable member.

In another preferred embodiment, the support member comprises first and second members slideably affixed to each other. The two members are configured to lift the breast when slid towards each other. In this case, an optional cushioning member may be disposed on the inner surfaces of the first and second members.

The medical device holder may be mounted to the breast immobilizer, and may be detachable. It can be mounted in such a fashion that it is rotatable. In addition, it can include a locking mechanism.

In accordance with an eighth aspect of the present invention, a method of performing a medical procedure on target tissue of a patient's breast is provided. The method comprises having the patient lie supine, immobilizing the breast and moving the target tissue away from the patient's chest wall with an immobilizing member while the patient is supine, and inserting a medical probe into the breast in contact with the target tissue. In one preferred method, the immobilizing member comprises a vacuum housing, and the breast is immobilized and the target tissue is moved away from the patient's chest wall by placing the breast within a cavity of a vacuum housing, and removing air from the cavity. In another preferred method, the immobilizing member comprises a support member, and the breast is immobilized and the target tissue is moved away from the patient's chest wall by constraining the base of the breast within a support member. In this case, the support member may comprise an expandable member, in which case, the base of the breast may be constrained by expanding the expandable member. The expandable member can be an inflatable member, and the inflatable member can be inflated by conveying a medium into the inflatable member. For example, the medium can be air or a saline solution.

Alternatively, the support member may comprise at least two slideable members, and the base of the breast can be constrained by sliding the at least two members towards each other. In this case, the method may optionally include cushioning the breast between the at least two slideable members.

Prior to guiding the medical probe into the breast, the medical probe may be rotated about the breast immobilizer and fixed relative to the breast immobilizer. The medical probe can be guided into the breast in registration with the breast immobilizer.

In one preferred method, the target tissue is ablated with the medical probe. In another preferred method, a sample of the target tissue is taken with a biopsy needle. Once the ablating or sampling is complete, the medical probe may be removed from the breast.

BRIEF DESCRIPTION OF THE DRAWINGS

The drawings illustrate the design and utility of a preferred embodiment of the present invention, in which similar elements are referred to by common reference numerals. In order to better appreciate the advantages and objects of the present invention, reference should be made to the accompanying drawings that illustrate this preferred embodiment. However, the drawings depict only one embodiment of the invention, and should not be taken as limiting its scope. With this caveat, the invention will be described and explained with additional specificity and detail through the use of the accompanying drawings in which:

FIG. 3 is a perspective view of an ablation probe assembly used in the tissue ablation system of FIG. 1, wherein a needle electrode array is particularly shown deployed;

FIG. 4 is a side view of a vacuum operated breast immobilization assembly used in the tissue ablation system of FIG. 1;

DETAILED DESCRIPTION OF THE PREFERRED EMBODIMENTS

Figure 1:
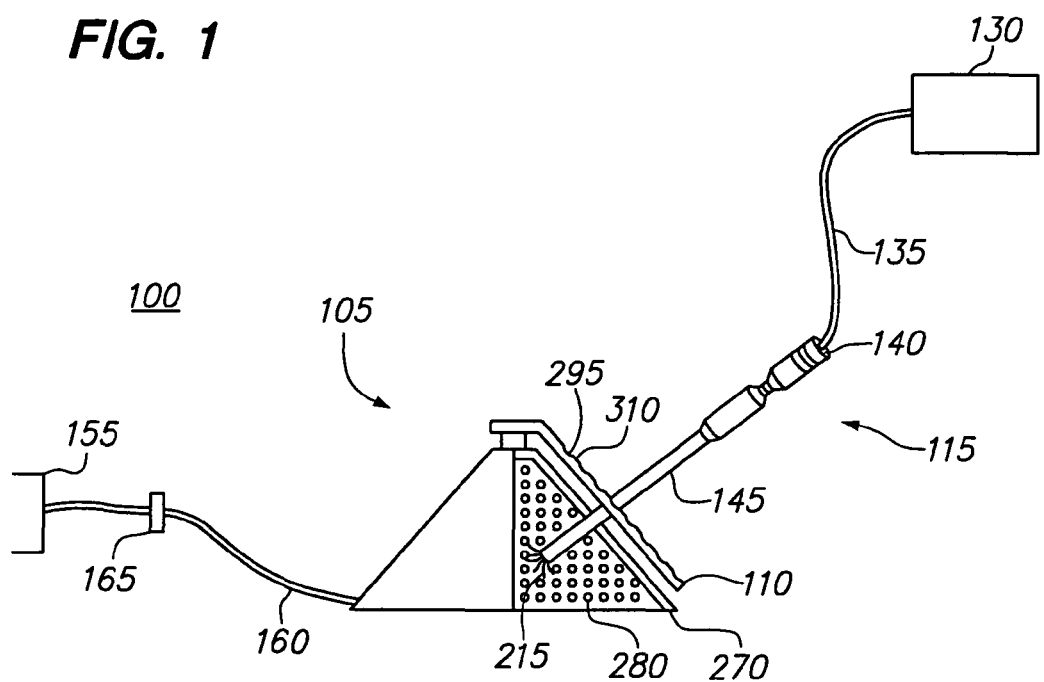
FIG. 1 is a plan view of a breast tissue ablation system constructed in accordance with a preferred embodiment of the present inventions.

FIG. 1 illustrates a breast tissue ablation system 100 constructed in accordance with a preferred embodiment of the present invention. The ablation system 100 generally comprises an ablation probe assembly 115, configured for introduction into a breast of a patient to ablate target tissue, such as a tumor, a radio frequency (RF) generator 130 configured for supplying RF energy to the probe assembly 115 in a controlled manner, and a vacuum operated breast immobilization assembly 105 configured to lift the breast away from the patient's body and stabilize it relative to an associated medical device holder 110.

Figure 2:
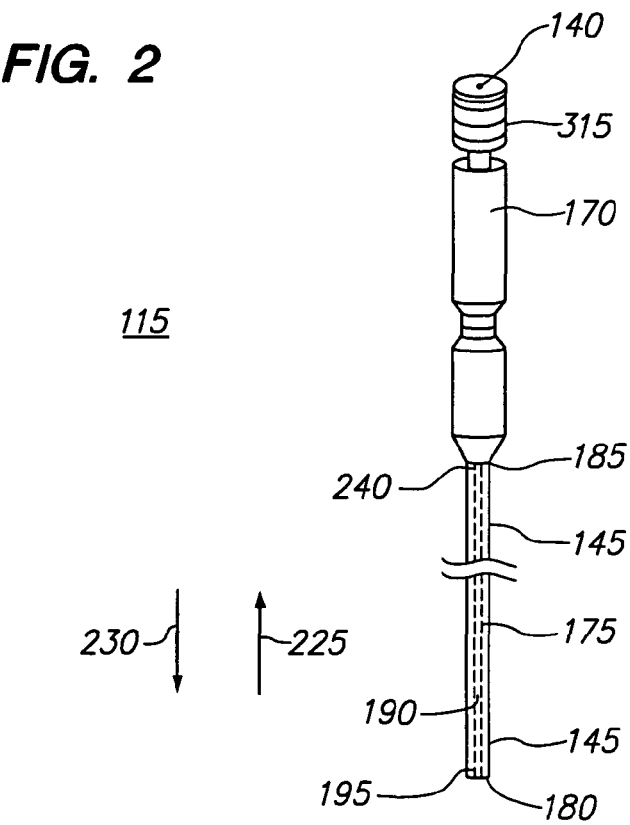
FIG. 2 is a perspective view of an ablation probe assembly used in the tissue ablation system of FIG. 1, wherein a needle electrode array is particularly shown retracted.

Referring specifically to FIGS. 2 and 3, the probe assembly 115 generally comprises a handle assembly 170, an elongated cannula 145, and an inner probe 175 slideably disposed within the cannula 145. The handle assembly 170 is mounted to the cannula 145. As will be described in further detail below, the cannula 145 serves to deliver the active portion of the inner probe 175 to the target tissue. The cannula 145 has a proximal end 185, a distal end 180, and a central lumen 190 extending through the cannula 145 between the proximal end 185 and the distal end 180. The cannula 145 may be rigid, semi-rigid, or flexible depending upon the designed means for introducing the cannula 145 to the target tissue. The cannula 145 is composed of a suitable material, such as plastic or metal, and has a suitable length, typically in the range of 5 cm to 30 cm, preferably from 10 cm to 20 cm. The cannula 145 has an outside diameter consistent with its intended use, typically being from 1 mm to 5 mm, usually from 1.3 mm to 4 mm. The cannula 145 has an inner diameter in the range of 0.7 mm to 4 mm, preferably from 1 mm to 3.5 mm.

The inner probe 175 comprises a reciprocating shaft 195 having a proximal end 205 and a distal end 210, and an array 215 of tissue penetrating needle electrodes 220 extending from the distal end 210 of the shaft 195. Like the cannula 145, the shaft 195 is composed of a suitable material, such as plastic or metal. The electrode array 215 can be mounted anywhere on the shaft 195. However, the electrodes 220 will typically be fastened to the shaft 195 at the shaft's distal end 210, though the individual electrodes 220 can extend up to the shaft's proximal end 205. Each of the needle electrodes 220 is a small diameter metal element, which can penetrate into tissue as it is advanced into a target site within the target region 125.

As illustrated in FIG. 2, longitudinal translation of the shaft 195 in the proximal direction 225 relative to the cannula 145, retracts the electrode array 215 into the distal end 180 of the cannula 145. When retracted within the cannula 145, the electrode array 215 is placed in a radially collapsed configuration, and each needle electrode 220 is constrained and held in a generally axially aligned position within the cannula 145 to facilitate its introduction into the tissue target site. The probe assembly 115 optionally includes a core member (not shown) mounted on the distal tip 210 of the shaft 195 and disposed within the center of the needle electrode array 215. In this manner, substantially equal circumferential spacing between adjacent needle electrodes 220 is maintained when the array is retracted within the central lumen 190 of the cannula 145.

As shown in FIG. 3, longitudinal translation of the shaft 195 in the distal direction 230 relative to the cannula 145 deploys the electrode array 215 out of the distal end 180 of the cannula 145. As will be described in further detail, manipulation of the handle assembly 170 will cause the shaft 195 to longitudinally translate to alternately retract and deploy the electrode array 215.

When deployed from the cannula 145, the electrode array 215 is placed in a three-dimensional configuration that usually defines a generally spherical or ellipsoidal volume having a periphery with a maximum radius in the range of 0.5 cm to 7 cm. The needle electrodes 220 are resilient and pre-shaped to assume a desired configuration when advanced into tissue. In the illustrated embodiment, the needle electrodes 220 diverge radially outwardly from the cannula 145 in a uniform pattern, i.e., with the spacing between adjacent needle electrodes 220 diverging in a substantially uniform pattern or symmetric pattern or both. In the illustrated embodiment, the needle electrodes 220 evert proximally, so that they face partially or fully in the proximal direction 225 when fully deployed. In exemplary embodiments, pairs of adjacent needle electrodes 220 can be spaced from each other in similar or identical, repeated patterns that can be symmetrically positioned about an axis of the shaft 195. It will be appreciated by one of ordinary skill in the art that a wide variety of patterns can be used to uniformly cover the region to be treated. It should be noted that although six needle electrodes 220 are illustrated in FIGS. 1 and 3, fewer needle electrodes 220 can be used or additional needle electrodes 220 can be added in the spaces between the illustrated electrodes 220, with the maximum number of needle electrodes 220 determined by the electrode width and total circumferential distance available. Thus, the needle electrodes 220 could be quite tightly packed.

Each electrode 220 is preferably composed of a single wire that is formed from resilient conductive metals having a suitable shape memory. Many different metals such as stainless steel, nickel-titanium alloys, nickel-chromium alloys, and spring steel alloys can be used for this purpose. The wires may have circular or non-circular cross-sections, but they preferably have rectilinear cross-sections. When constructed in this fashion, the needle electrodes 220 are generally stiffer in the transverse direction and more flexible in the radial direction. The circumferential alignment of the needle electrodes 220 within the cannula 145 can be enhanced by increasing transverse stiffness. Exemplary needle electrodes will have a width in the circumferential direction in the range of 0.2 mm to 0.6 mm, preferably from 0.35 mm to 0.40 mm, and a thickness, in the radial direction, in the range of 0.05 mm to 0.3 mm, preferably from 0.1 mm to 0.2 mm.

The distal ends 235 of the needle electrodes 220 may be honed or sharpened to facilitate their ability to penetrate tissue. The distal ends 235 of these needle electrodes 220 may be hardened using conventional heat treatment or other metallurgical processes. The needle electrodes 220 may be partially covered with insulation, although they will be at least partially free from insulation over their distal portions 235. The proximal ends 240 of the needle electrodes 220 may be directly coupled to the proximal end 205 of the shaft 195, or alternatively, may be indirectly coupled thereto via other intermediate conductors such as RF wires. Optionally, the shaft 195 and any components between the shaft 195 and the needle electrodes 220 are composed of an electrically conductive material such as stainless steel, and may therefore conveniently serve as intermediate electrical conductors.

In the illustrated embodiment, the RF current is delivered to the electrode array 215 in a mono-polar fashion. Therefore, the current will pass through the electrode array 215 and into the target tissue 125, thus inducing necrosis in the tissue. To this end, the electrode array 215 is configured to concentrate the energy flux in order to have an injurious effect on tissue. However, there is a dispersive electrode (not shown) which is located remotely from the ablation electrodes 220, and has a sufficiently large area—typically 130 $cm^2$ for an adult—so that the current density is low and non-injurious to the surrounding tissue. In the illustrated embodiment, the dispersive electrode may be attached externally to the patient, using a contact pad placed on the patient's skin. In a mono-polar arrangement, the needle electrodes 220 are bundled together with their proximal portions 240 having only a single layer of insulation over the entire bundle.

Alternatively, the RF current is delivered to the electrode array 215 in a bipolar fashion, which means that current will pass between positive and negative electrodes 220 within the array 215. In a bipolar arrangement, the positive and negative needle electrodes 220 will be insulated from each other in any regions where they would or could be in contact with each other during the power delivery phase.

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

The probe assembly 115 may optionally have active cooling functionality, in which case, a heat sink (not shown) can be mounted within the distal end 210 of the shaft 195 in thermal communication with the electrode array 215, and cooling and return lumens (not shown) can extend through the shaft 195 in fluid communication with the heat sink to draw thermal energy away and back to the proximal end 205 of the shaft 195. A pump assembly (not shown) can be provided to convey a cooling medium through the cooling lumen to the heat sink, and to pump the heated cooling medium away from the heat sink and back through the return lumen. Further details regarding active cooling of the electrode array 215 are disclosed in co-pending U.S. application Ser. No. 10/387,812, which is hereby expressly incorporated herein by reference.

Referring back to FIG. 1, the RF generator 130 is electrically connected, via a generator connector 140, to the handle assembly 170, which is directly or indirectly electrically coupled to the electrode array 215. The RF generator 130 is a conventional RF power supply that operates at a frequency in the range of 200 KHz to 1.25 MHz, with a conventional sinusoidal or non-sinusoidal wave form. Such power supplies are available from many commercial suppliers, such as Valleylab, Aspen, and Bovie. Most general purpose electro-surgical power supplies, however, operate at higher voltages and powers than would normally be necessary or suitable for controlled tissue ablation.

Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as RadioTherapeutics of San Jose, Calif., which markets these power supplies under the trademarks RF2000™ (100 W) and RF3000™ (200 W).

Figure 5:
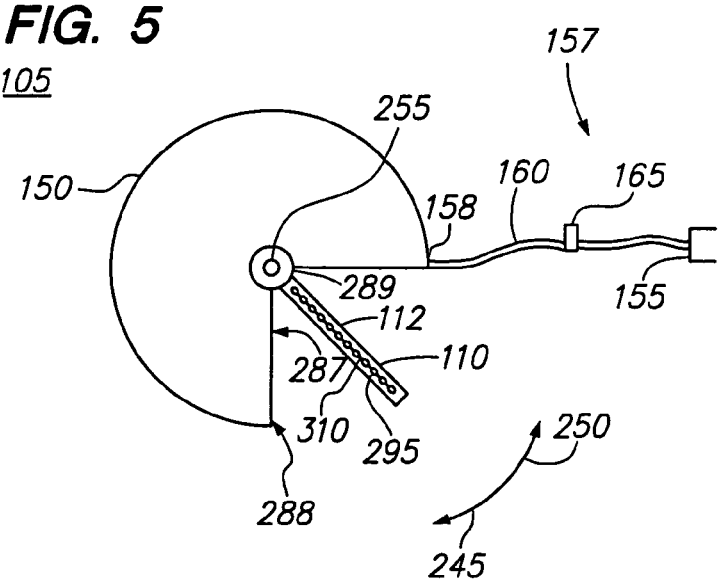
FIG. 5 is a top view of the vacuum operated breast immobilization assembly of FIG. 4.

Referring now to FIGS. 4 and 5, the breast immobilization assembly 105 comprises a vacuum housing 150, a vacuum assembly 157, and a rotating medical device holder 110.

In the illustrated embodiment, the vacuum housing 150 takes the form of a cup shaped such that it can be conveniently placed over and encompass a breast. In the illustrated embodiment, the cup 150 takes the form of a hollow cone having a breast cavity 287, an open end 288 to provide access to the breast cavity 287, and a closed vertex 289 opposite the open end 288, so that the breast cavity 287 is substantially air tight when a breast is placed within the breast cavity 287. Other suitable shapes, such as a pyramid or hemisphere, can also be used for the cup 150. The cup 150 is composed of a suitably rigid material. In the preferred embodiment, the cup 150 is composed of a radio-lucent material to permit monitoring of the medical treatment using, for example, a computerized axial tomography scanner (not shown) or a magnetic resonance imaging device (also not shown). In order to provide access to the breast, a one-quarter section of the cup 150 is removed in order to form a three-quarter cup 150, as best shown in FIG. 5. Depending upon the level of breast access desired by the physician, a larger or smaller section can be removed from the cup 150. For example, a one-half or one-quarter cup can be used.

Because there is significant variation in breast size and shape within the general population, the breast immobilization cup 150 can be made in various sizes and shapes to accommodate breast variation. Thus, the cup 150 can be made to be detachable from the breast immobilizing assembly 105, so that an incorrectly sized cup 150 can be removed and a correctly sized cup 150 can be attached in its place. In addition, the cup 150 can be made for either a one time use—i.e., disposable—or for multiple uses. When the cup 150 is made to be reused it is constructed of material that can withstand standard sterilization techniques—autoclave sterilization, chemical sterilization, etc.

Figure 6:
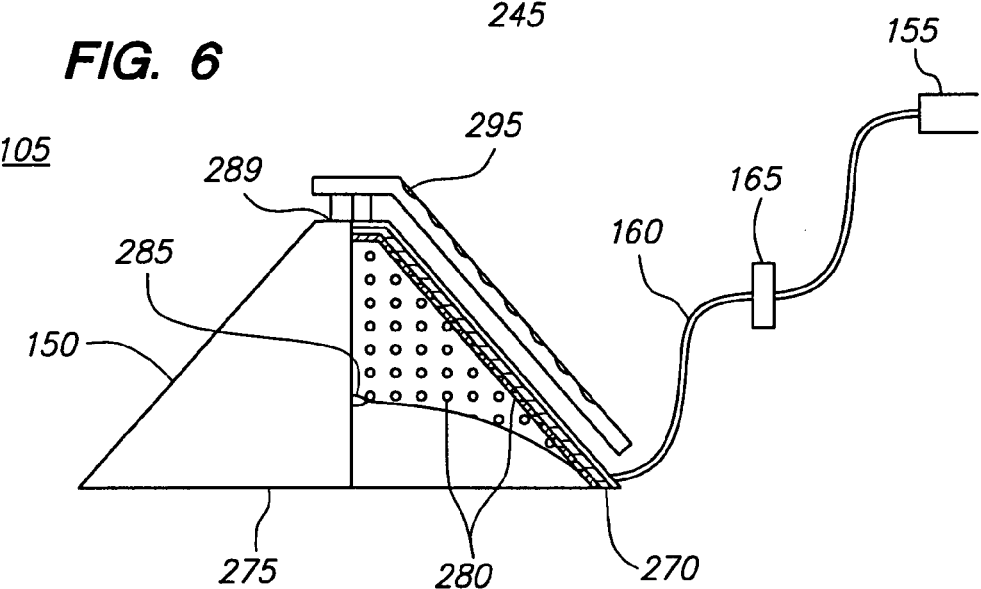
FIGS. 6-8 and 10 are views showing the operation of the tissue ablation system of FIG. 1 in ablating tissue within a breast.
Figure 7:
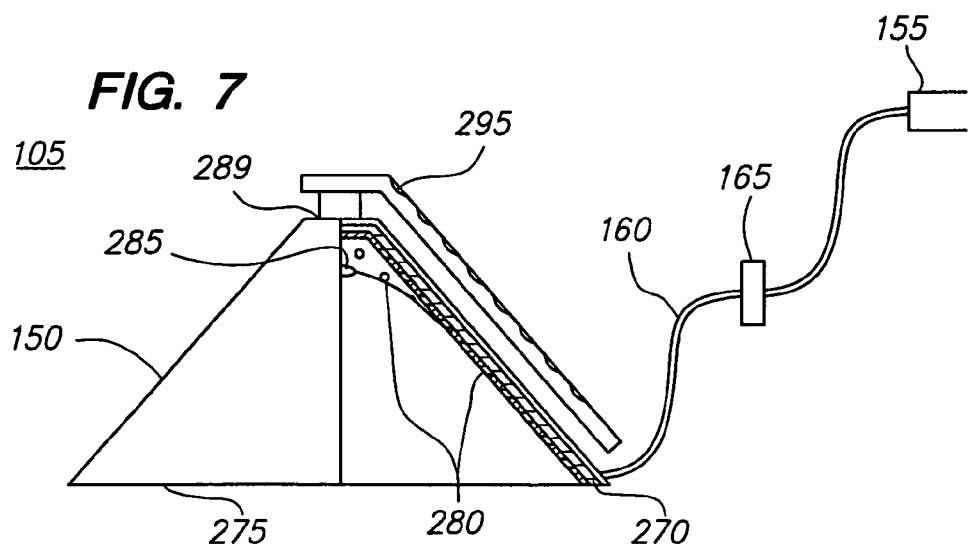

The cup 150 comprises an outer wall 260, an inner wall 265, and a thin chamber 270—shown in phantom in FIGS. 4, 6, and 7—formed between the outer and inner walls 260 and 265. The cup 150 comprises a plurality of uniformly spaced holes 280 that extend through the inner wall 265 in communication with the chamber 270. As will be described in further detail below, the holes 280 serve to focus vacuum pressure within the breast cavity 287. It should be noted that other types of openings for focusing the vacuum pressure can also be used. For example, channels can be formed through inner wall 265.

The vacuum assembly 157 comprises a vacuum source 155, a vacuum hose 160, and a check/relief valve 165. The vacuum source 155 can be any suitable vacuum source, for example, an operating room wall mounted vacuum. The vacuum hose 160 connects the vacuum source 155 to a vacuum port 158 that is located on the cup 150 and is in communication with the chamber 270. Thus, when the vacuum source 155 is operated, air is drawn into the holes 280, through the chamber 270, and then out through the vacuum hose 160 to the vacuum source 155. Thus, as will be discussed in further detail below, operation of the vacuum source 155 will cause a breast enveloped by the cup 150 to adhere to the inner wall 265.

In order to ensure a minimum of discomfort for the patient, the vacuum relief valve 165 is connected in line with the vacuum hose 160. The valve 165 permits some of the air to escape from the hose 160, so that the vacuum suction on the patient's breast is not so great that it causes any unnecessary discomfort. A default level of relief can be set by the manufacturer, with a control available on the valve 165, so that the physician can adjust the relief according to the special needs of the individual patient.

In the illustrated embodiment, the medical device holder 110 is attached to vertex 289 of the breast immobilization cup 150. As shown in FIGS. 4 and 5, the medical device holder 110 comprises an arm 112 that is rotatably mounted to the vertex 289 of the cup 150, so that it can be selectively rotated in a clockwise direction 245 or a counterclockwise direction 250. Thus, the treating physician will be able to conveniently position the medical device holder 110 directly over the point of entry into the breast. The medical device holder 110 further comprises a locking mechanism 255 for locking the arm 112 in place. In the illustrated embodiment, the locking mechanism 255 takes the form of a tightening screw. Other types of locking mechanisms, such as a tightening clamp, can be used as well without departing from the spirit of the present invention.

Figure 9:
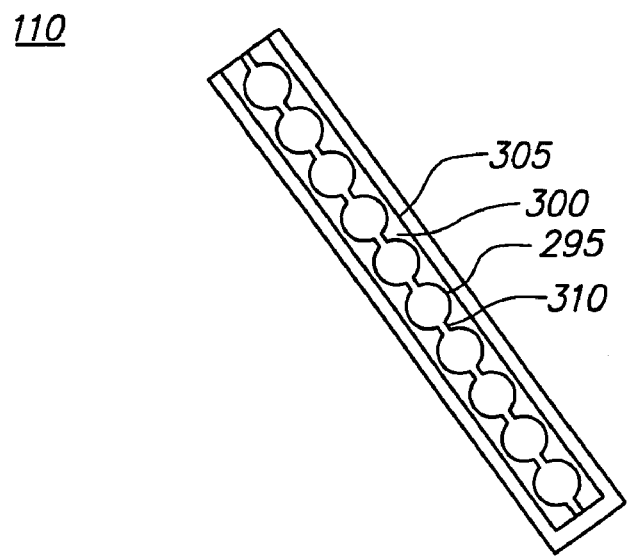
FIG. 9 is a top view of a preferred embodiment of a medical device holder used in the vacuum operated breast immobilization assembly of FIG. 4.

As best shown in FIG. 5, the medical device holder 110 comprises a plurality of holes 295 uniformly spaced along the length of the arm 112. In particular, as illustrated in FIG. 9, the holder arm 112 has an open channel 305 formed along the length of the arm 112, and a compliant membrane 300, such as, for example, silicone, that lines the open channel. The holes 295 are spaced along the length of the compliant membrane 300. The holes 295 are large enough to insert the ablation probe cannula 145 through the arm 112, but small enough so that the cannula 145 is held in place once it is inserted into a hole 295. The holder 110 further comprises optional slits 310 that connect the holes 295, thereby enabling the physician to move the cannula 145 from one hole 295 to its neighbor by simply sliding it through the slit 310 that connects the two holes 295 to each other. Thus, the physician need not completely withdraw the cannula 145 from the holder 110 in order to move it from one hole 295 to another. This feature makes it possible to make quick adjustments during the medical treatment.

Figure 16:
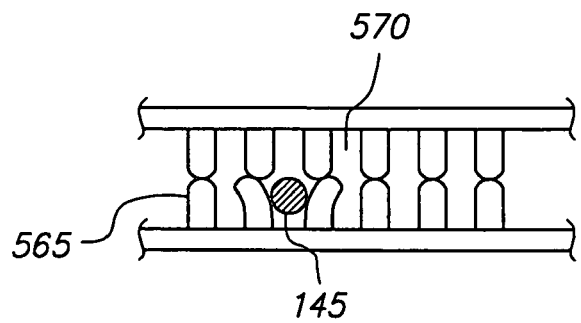
FIG. 16 is a cutaway top view of another preferred embodiment of a medical device holder that can be used in the breast tissue ablation system of FIG. 1.

It should be noted that other types of medical device holders can be used. For example, referring to FIG. 16, another preferred embodiment of a medical device holder 610 is described. The medical device holder 610 is similar to the medical device holder 110 described above in that it includes a rigid arm 112 with an open channel 305. The medical device holder 610 differs, however, in that, rather than a silicone membrane 300 with holes 295, a pair of opposing sets of compliant fingers 565 extend along the inside surfaces of the arm 112, so that they straddle the open channel 305. The ends of the first set of fingers 565 are in contact with the ends of the second set of fingers 565, such that continuous spaces 570 are formed between neighboring pairs of opposing fingers 565, as illustrated in FIG. 16.

Thus, the cannula 145 can be introduced into the holder 610 through an appropriate space 570 between adjacent fingers 565. The compliance of the opposing fingers 565 enables the physician to move the cannula 145 from one space 570 to its neighbor by simply sliding the device between the opposing fingers 565 that separate the two adjacent spaces 570. Thus, the physician need not withdraw the cannula 145 from the holder 610 in order to move it from one space 570 to another. This feature makes it possible to make fast adjustments during the medical treatment.

Figure 17:
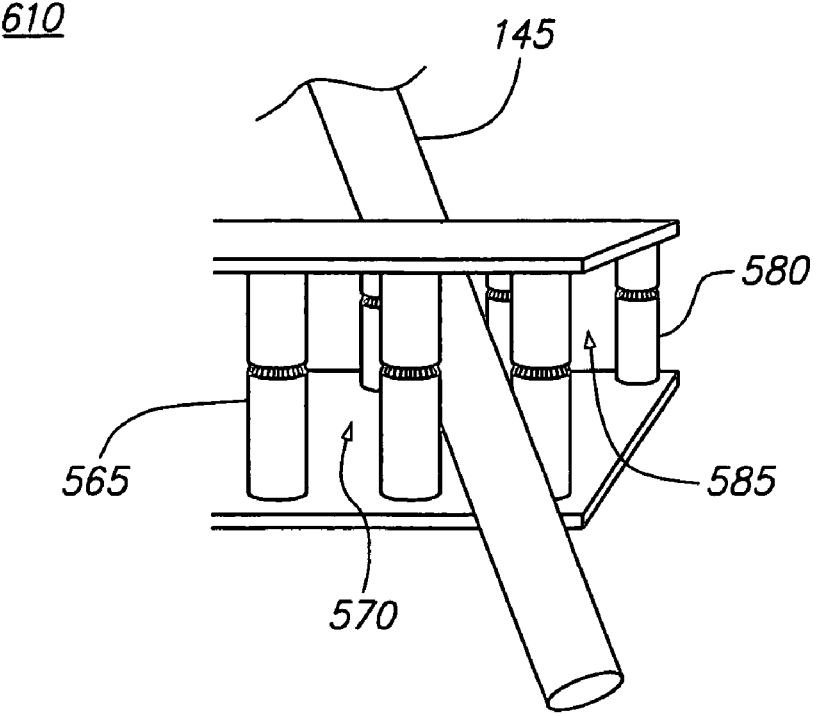
FIG. 17 is a cutaway perspective view of still another preferred embodiment of a medical device holder that can be used in the breast tissue ablation system of FIG. 1.

FIG. 17 illustrates an optional feature of the medical device holder 610. In particular, the medical device holder 610 may comprise additional opposing sets of compliant fingers 580 that extend along the inside surfaces of the arm 112 in a parallel relationship with the first opposing sets of compliant fingers 565. Thus, a first set of continuous spaces 570 is formed by the first opposing sets of compliant fingers 565, and a second set of continuous spaces 585 is formed by the second opposing sets of compliant fingers 580. Thus, when a cannula 145 is inserted into the holder 610, it can be aimed more accurately through judicious choice of both the first set of spaces 570 and second set of spaces 585. For example, the cannula 145 can be inserted through the holder 110 at an angle in a stable manner, by inserting it through one of the first set of spaces 570, and then inserting it through one of the second set of spaces 585 that is obliquely situated in relation to the first space 570, as illustrated in FIG. 17.

Once the holder 110 is locked in place, the ablating probe cannula 145 can be pushed through the appropriate hole 295 (or space 570 between sets of opposing fingers 565, as the case may be) and into the breast without a loss of control due to holder 110 rotation. Thus, the medical probe cannula 145 is guided into the breast in registration with the vacuum housing 150 by using the medical device holder 110 that is attached to the vacuum housing 150. The use of the compliant membrane 300 to line the holder 110 (or fingers 565) serves at least two purposes. First, it provides protection for the cannula 145 so that it does not get scratched as it goes through the holder 110. Second, the compliancy of the membrane 300 (or fingers 565) allows for some play, so that the physician can make adjustments to the angle of the cannula 145 during treatment. However, it should be noted that the holes 295 (or spaces 570 between fingers 565) should be made small enough so that when the cannula 145 is pushed through one of the holes 295 (or spaces 570 between fingers 565), it does not wiggle around, but remains in a relatively stable state until manipulated by the physician.

Referring now to FIGS. 6, 7, 8, and 10, one preferred method of using the breast tissue ablation system 100 to perform an ablation of a patient's breast 120 is provided. The procedure is performed on a patient while she lies supine. As illustrated in FIG. 6, the physician places the breast immobilizing cup 150 on the breast 120, so that the cup 150 partially surrounds the complement of that portion of the breast 120 upon which the ablation is to be performed, while leaving the portion to be treated exposed. In the illustrated embodiment, the cup 150 is placed on the breast 120 so that the vertex 289 lies directly above the nipple 285. The cup 150, however, can be placed on other areas on the breast 120, depending on the location of the target breast tissue 125. Once the immobilizing cup 150, which is connected to the vacuum generating source 155 via the vacuum hose 160, is properly situated on the breast, the vacuum source 155 is operated to partially evacuate the space between the breast immobilizing cup 150 and the breast 120 by drawing air from this space, through the holes 280, through the chamber 270, and into the vacuum hose 160. As illustrated in FIG. 7, this partial vacuum causes the breast 120 to adhere to the cup 150, which simultaneously lifts the breast 120 up from the patient's body.

Figure 8:
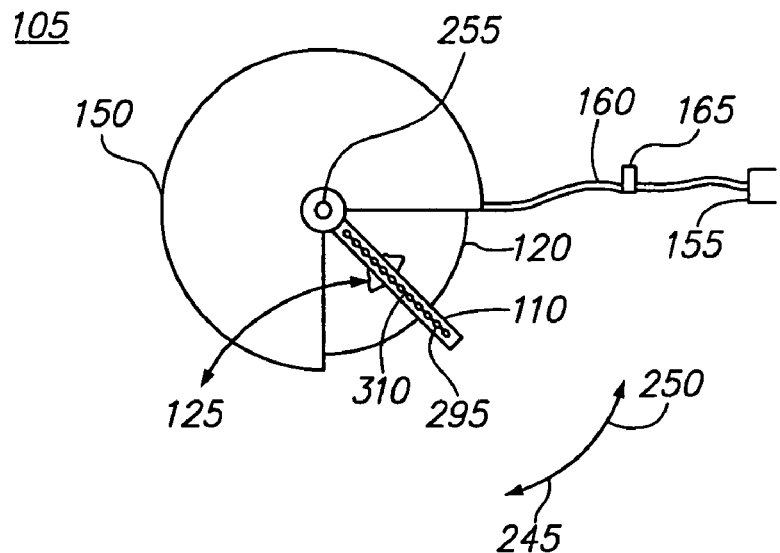
Figure 10:
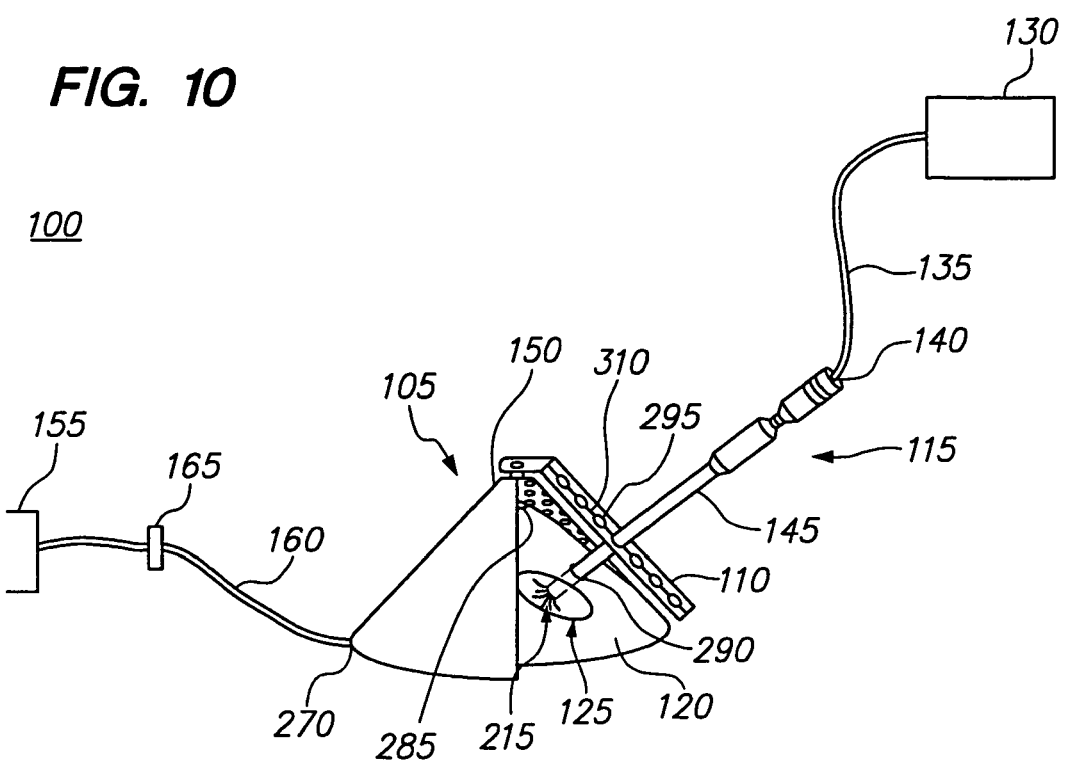

As illustrated in FIG. 8, the medical device holder 110 is rotated until it lies above the target area 125 in the breast where an ablation probe 115 is to be used, and then locked in place using a locking mechanism 255. Next, as illustrated in FIG. 10, the ablation probe cannula 145 is inserted into an appropriate hole 295 in the medical device holder 110, and the cannula 145 is pushed through the hole 295, through the point of entry 290 into the breast 120, and into the target breast tissue 125. The position of the cannula 145 with respect to the target breast tissue 125 can be monitored by suitable means, such as, for example, computerized axial tomography, magnetic resonance imaging, or ultrasound imaging. If during the procedure it is determined that the cannula 145 should be in a hole 295 adjacent to the hole 295 in which it was inserted, the cannula 145 can be slid through a slit 310 connecting the two holes 295, and into the adjacent hole 295. Thus, the medical probe cannula 145 is guided into the breast in registration with the vacuum housing 150 by using the medical device holder 110 that is attached to the immobilizing cup 150. Once the cannula 145 reaches the target tissue 125, the electrode array 215 is deployed into the target tissue 125, and RF energy is introduced into the target tissue 125 to induce tissue necrosis, as illustrated in FIG. 10. The ablation procedure can be repeated for different locations within the target breast tissue 125 by retracting the electrode array 215 within the cannula 145, introducing the cannula 145 into other holes 295 in the medical device holder 110, deploying the electrode array 215, and ablating.

Figure 11:
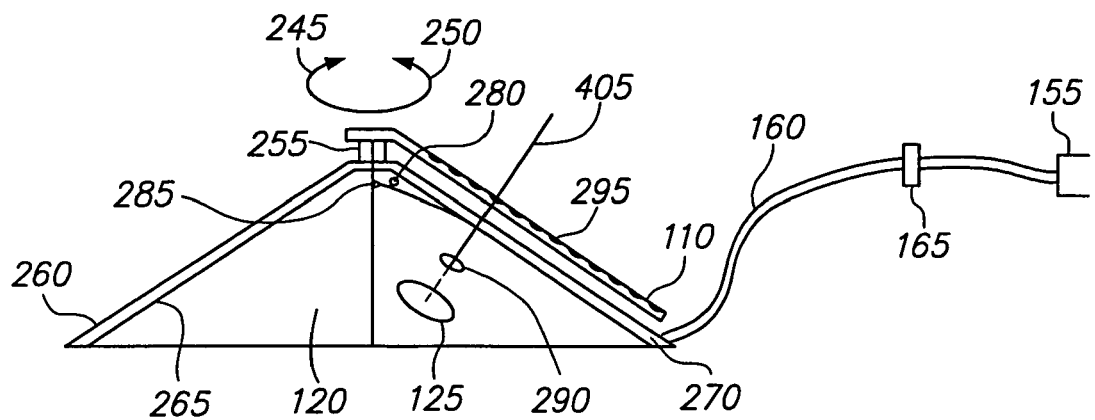
FIG. 11 is a side view showing a biopsy using the breast immobilization assembly of FIG. 4.

It should be noted that although the breast immobilization assembly 105 has been discussed in the context of an ablation system, it can be used in other types of systems. For example, referring to FIG. 11, the breast immobilization assembly 105 is used with a biopsy needle 405 for taking a tissue biopsy. The breast immobilization assembly 105 can also be used, for example, with a "loc" needle used for locating a tumor or other abnormality. The biopsy procedure is similar to the previously described procedure, with the exception that no ablation treatment takes place. Instead, once the biopsy needle 405 reaches the target tissue 125, a portion of the target tissue 125 is removed using the biopsy needle 405. The sample can then be tested to determine whether or not the tissue is cancerous. It should also be noted that other types of ablation probes can be used to treat the breast tissue. For example, rather than a probe with an ablation array, a probe with a single needle electrode can be used. Also, probes that utilize other types of ablation energy, e.g., laser ablation, cryoablation, and microwave ablation, can be utilized to treat the breast tissue. In addition, probes that deliver radiation elements to the breast tissue can also be utilized.

The various embodiments of the present invention solve a problem associated with performing ablation (or biopsy or irradiation, etc.) on a breast. Since the embodiments lift the breast up and away from the chest wall, the tissue abnormality to be treated is also lifted away from the chest wall. This reduces the possibility of damage to the neighboring costochondral wall and the surrounding healthy tissue. In addition, since the compressive effects of gravity are overcome, the abnormality is not as close to the skin surface, so the risk of dermal blistering is reduced.

Figure 12:
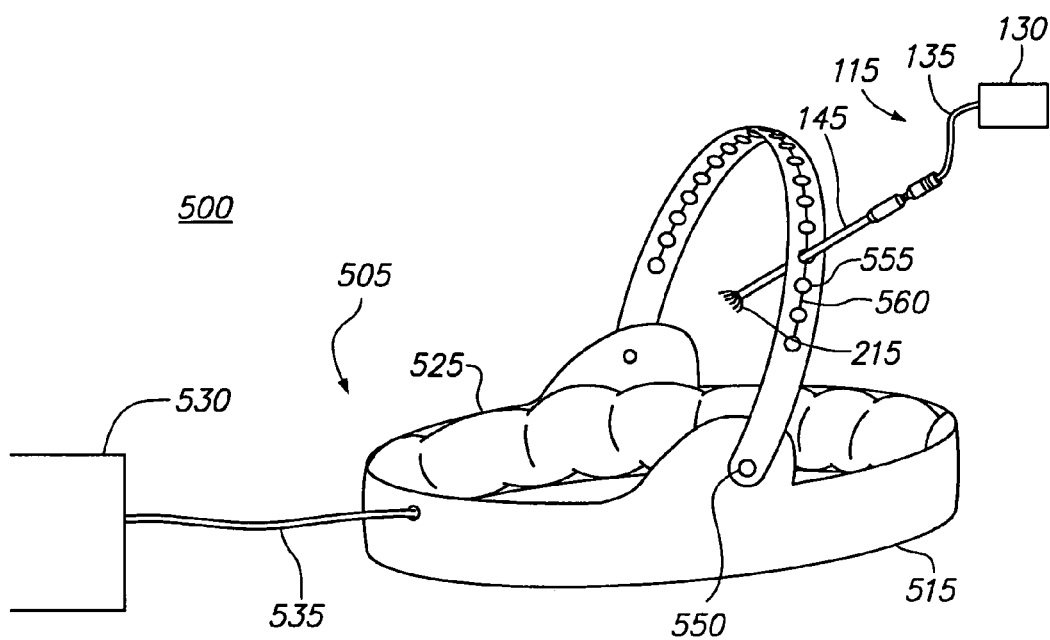
FIG. 12 is a plan view of a breast tissue ablation system constructed in accordance with another preferred embodiment of the present inventions.

FIG. 12 illustrates a breast tissue ablation system 500 constructed in accordance with another preferred embodiment of the present invention. The ablation system 500 generally comprises the previously described ablation probe assembly 115 and RF generator 130, and an expandable breast immobilization assembly 505 configured to lift a breast up and away from a patient's body.

Figure 13:
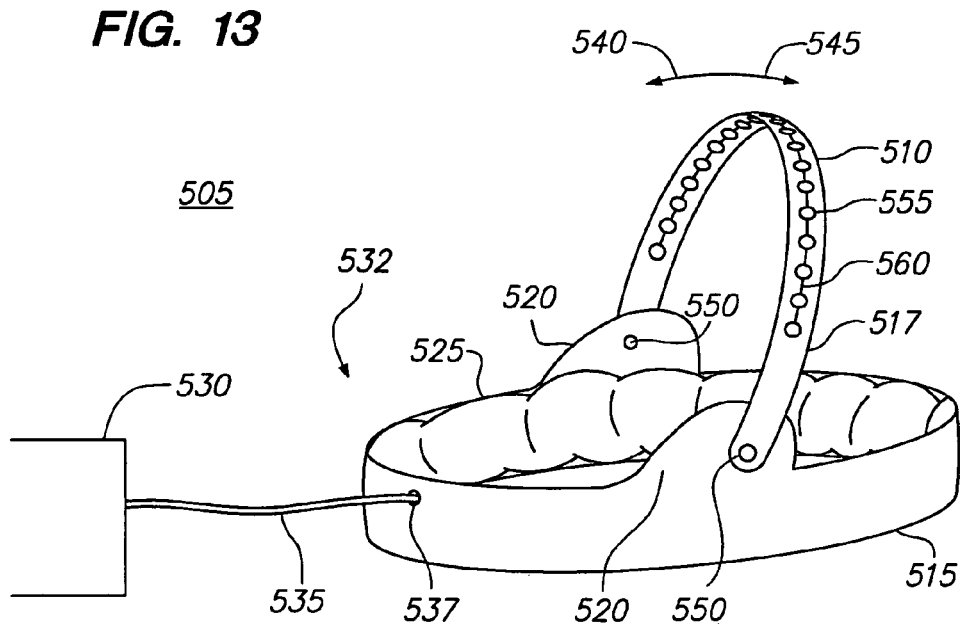
FIG. 13 is a side view of an inflatable breast immobilization assembly that can be used in the breast tissue ablation system of FIG. 12.
Figure 14:
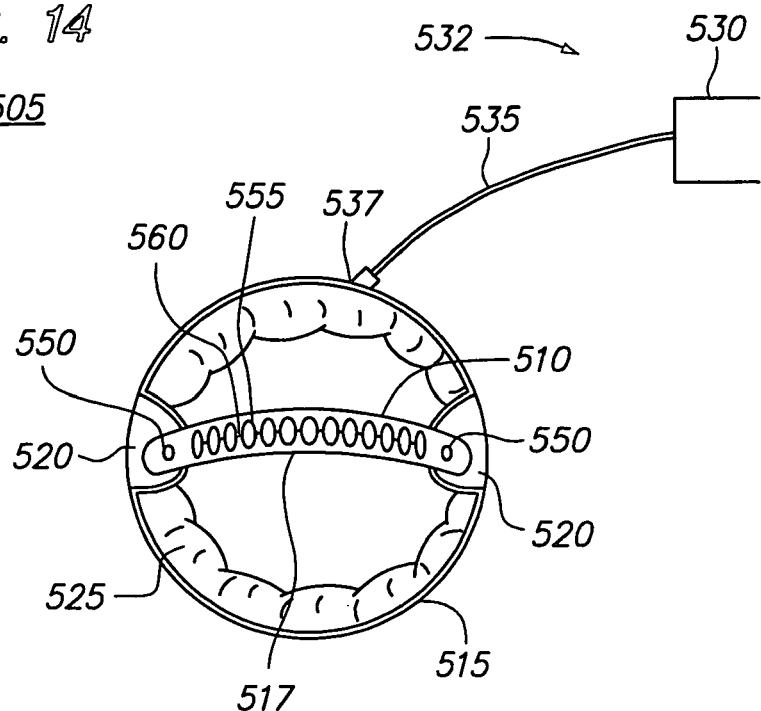
FIG. 14 is a top view of the inflatable breast immobilization assembly of FIG. 13.

Referring specifically to FIGS. 13 and 14, the breast immobilization assembly 505 comprises a hollow fixture 515, an expandable member 525 mounted on the interior of the fixture 515, a pump assembly 532 for filling the expandable member 525, and a medical device holder 510.

In the illustrated embodiment, the fixture 515 is shaped such that it can be conveniently placed over and encompass the base of a breast. In the illustrated embodiment, the fixture 515 takes the form of a circular ring, although other shapes such as, for example, an elliptic or oval ring, can be used. The fixture 515 is composed of a suitably rigid material, such as, for example, plastic or metal. In the preferred embodiment, the fixture 515 is composed of a radio-lucent material to permit monitoring of the medical treatment using, for example, a computerized axial tomography scanner (not shown) or a magnetic resonance imaging device (also not shown). In the illustrated embodiment, the expandable member 525 takes the form of an inflatable tube 525 composed of a non-compliant or compliant material—for example, rubber—and is suitably bonded to the inside surface of the fixture 515. It should be noted, however, that other forms of expandable members 525 can be used.

Because there is significant variation in breast size within the general population, the fixture 515 can be made in various sizes and shapes to accommodate breast variation. Thus, the fixture 515 can be made to be detachable from the rest of the breast immobilizing assembly 505, so that an incorrectly sized fixture 515 can be removed and replaced with a correctly sized fixture 515. In addition, the fixture 515 and the inflation tube 525 can be made for either a one time use—i.e., disposable—or for multiple uses. When either the fixture 515 or the tube 525 is made to be reused, it is constructed of material that can withstand standard sterilization techniques—autoclave sterilization, chemical sterilization, etc.

The pump assembly 532 comprises a pump 530 and a pump hose 535. The pump 530 can be any suitable pump, such as, for example, an operating room wall mounted pump. The pump hose 535 connects the pump 530 to the interior region of the inflatable member 525 via a port opening 537 in the fixture 515. Thus, when the pump 530 is operated, a suitable medium—for example, air or a saline solution—is conveyed through the pump hose 535 and into the inflatable member 525. In this manner, the inflatable member 525 is transformed from an unexpanded state as shown in FIG. 13 to an expanded state as shown in FIG. 14.

The medical device holder 510 is pivotally coupled to the fixture 515. In particular, the fixture 515 comprises two brackets 520 mounted to the fixture 515 in an antipodal relationship. The medical device holder 510 comprises a curved member 517 with opposing ends that are respectively mounted to the brackets 520 via hinged connections 550. Thus, the holder 510 can be selectively pivoted in a first direction 540 or a second opposite direction 545, thereby allowing the treating physician to conveniently position the medical device holder 510 directly over the point of entry into the breast. The medical device holder 510 further comprises a locking mechanism (not shown) for locking the curved member 517 in place. In the preferred embodiment, the locking mechanism takes the form of a tightening screw. Other types of locking mechanisms, such as a tightening clamp, can be used as well without departing from the spirit of the present invention. In addition, other designs can be used for connecting the medical device holder 510 to the fixture 515. For example, the fixture 515 need not have raised brackets 520 at the connections 550.

Figure 15:
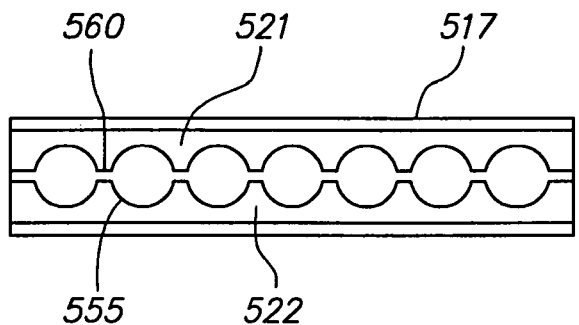
FIG. 15 is a top view of a preferred embodiment of a medical device holder that can be used in the breast tissue ablation system of FIG. 1.

As is best shown in FIG. 14, the holder 510 comprises a plurality of holes 555 uniformly spaced along the length of the curved member 517 in a manner similar to the way that the holes 295 were spaced long the length of the arm 112 of the previously described medical device holder 110. In particular, as illustrated in FIG. 15, the holder 510 has an open channel 521 formed along the length of the curved member 517, and a compliant material 522, such as, for example, silicone, that lines the open channel 521. The holes 555 are spaced along the length of the compliant material 522. Each hole 555 is large enough to insert the ablation probe cannula 145 through the curved member 517, but small enough so that the cannula 145 is held in place once it is inserted into the hole 555. The holder 510 further comprises optional slits 560 that connect the holes 555, thereby enabling the physician to move the cannula 145 from one hole 555 to its neighbor by simply sliding it through the slit 560 that connects the two holes 555 to each other, as previously described above with respect to the medical device holder 110.

It should be noted that other types of medical device holders can be used. For example, as previously described above with respect to the medical device holder 110, opposing silicone fingers can be used, as illustrated in FIGS. 16 and 17.

Figure 18:
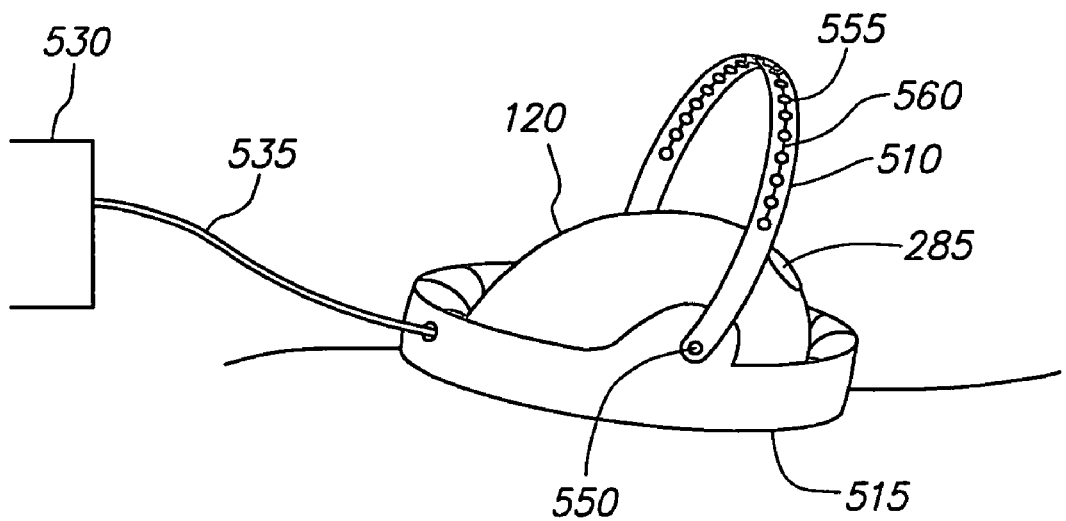
FIGS. 18-20 are views showing the operation of the tissue ablation system of FIG. 12 in treating tissue within a breast.
Figure 19:
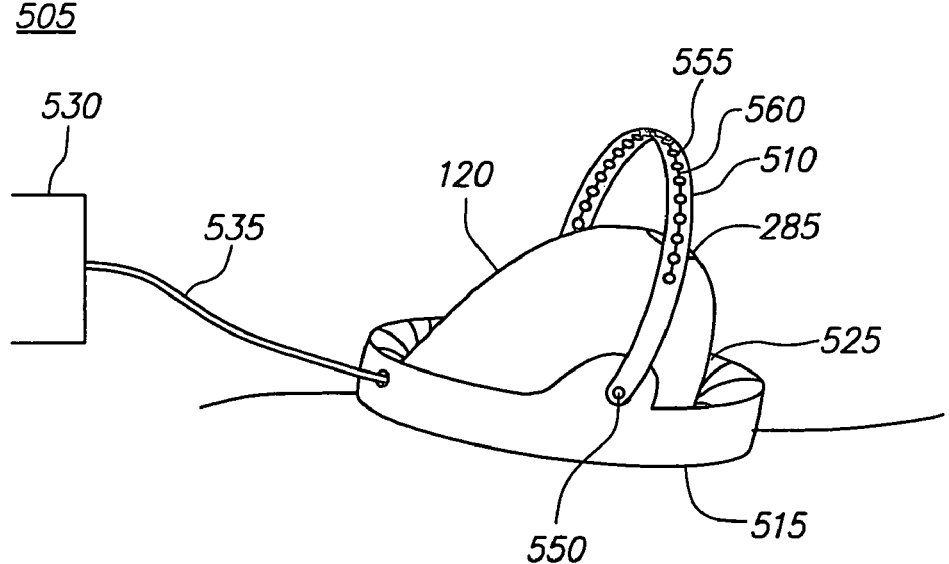
Figure 20:
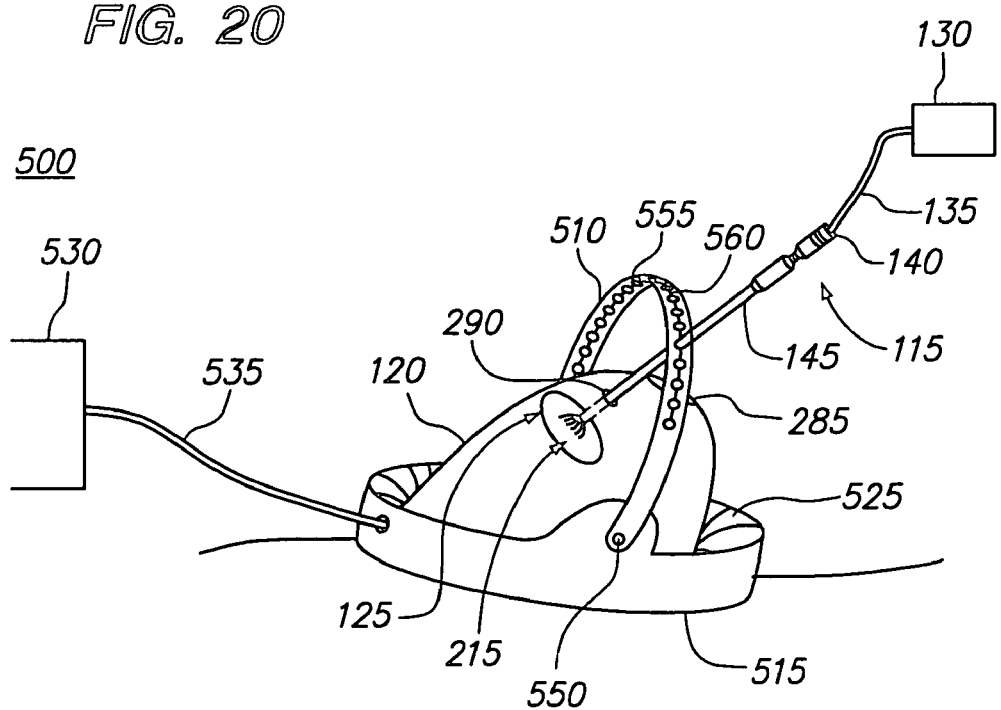

Referring now to FIGS. 18-20, one preferred method of using the breast tissue ablation system 500 to perform an ablation of a patient's breast 120 is provided. The procedure is performed on a patient lying supine. As illustrated in FIG. 18, while the inflatable tube 525 is in its deflated state, the physician places the breast immobilizing fixture 515 around the breast 120, so that the fixture 515 surrounds the base of the breast 120. The pump 530 is then operated to place the inflatable tube 525 in its inflated state, which in turn, lifts the breast 120 up and away from the patient's body, as illustrated in FIG. 19.

As illustrated in FIG. 20, the medical device holder 510 is pivoted until it lies above the target tissue area 125 or some other location deemed appropriate by the treating physician, and is then locked into place using the locking mechanism at either connection 550, or both connections 550, according to the predilection of the physician. Next, as illustrated in FIG. 20, the ablating probe cannula 145 is inserted into the appropriate hole 555 in the medical device holder 510, and the cannula 145 is pushed through the hole 555, through the entry point 290 on the surface of the breast 120, and into the target breast tissue 125. Thus, the cannula 145 is guided into the breast in registration with the breast immobilizing fixture 515. The position of the cannula 145 with respect to the target breast tissue 125 can be monitored by suitable means, such as, for example, computerized axial tomography, magnetic resonance imaging, or ultrasound imaging. Once, the cannula 145 reaches the target tissue 125, the electrode array 215 is deployed into the target region 125, and RF energy is introduced into the target tissue 125 to induce tissue necrosis. The ablation procedure can be repeated for different locations within the target breast tissue 125 by retracting the electrode array 215 within the cannula 145, introducing the cannula 145 into other holes 555, deploying the electrode array 215, and ablating.

Figure 21:
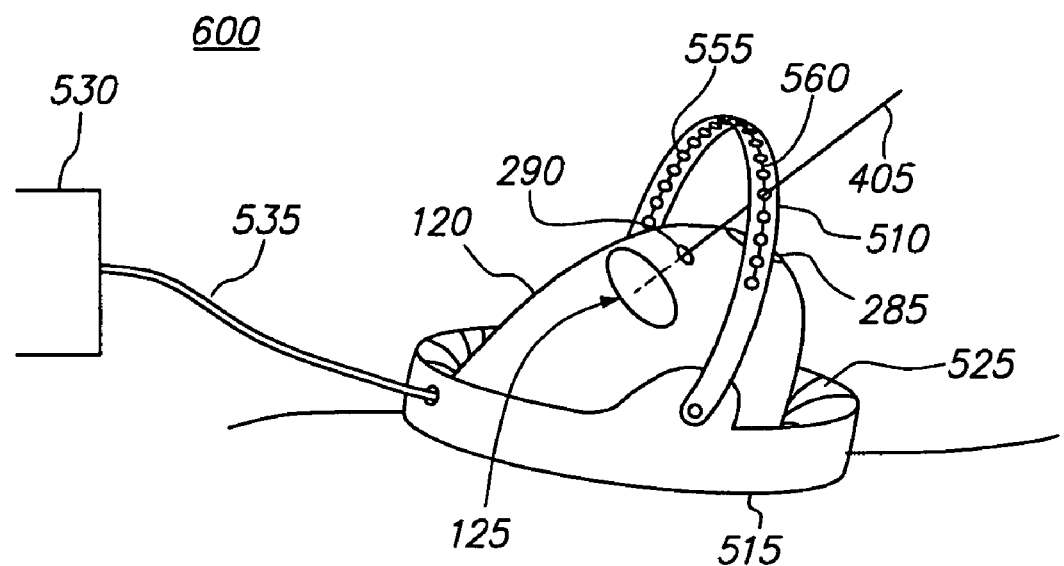
FIG. 21 is a side view of a biopsy using the breast immobilization assembly of FIG. 13.

It should be noted that although the breast immobilization assembly 505 has been discussed in the context of an ablation system, it can be used in other types of systems. For example, referring to FIG. 21, the breast immobilization assembly 505 is used with a biopsy needle 405 for taking a tissue biopsy. The breast immobilization assembly 505 can also be used, for example, with a "loc" needle for locating a tumor or other abnormality. The biopsy procedure is similar to the previously described procedure, with the exception that no ablation treatment takes place. Instead, once the biopsy needle 405 reaches the target tissue 125, a portion of the target tissue 125 is removed using a biopsy needle 405. The sample can then be tested to determine whether or not the tissue is cancerous.

Figure 22:
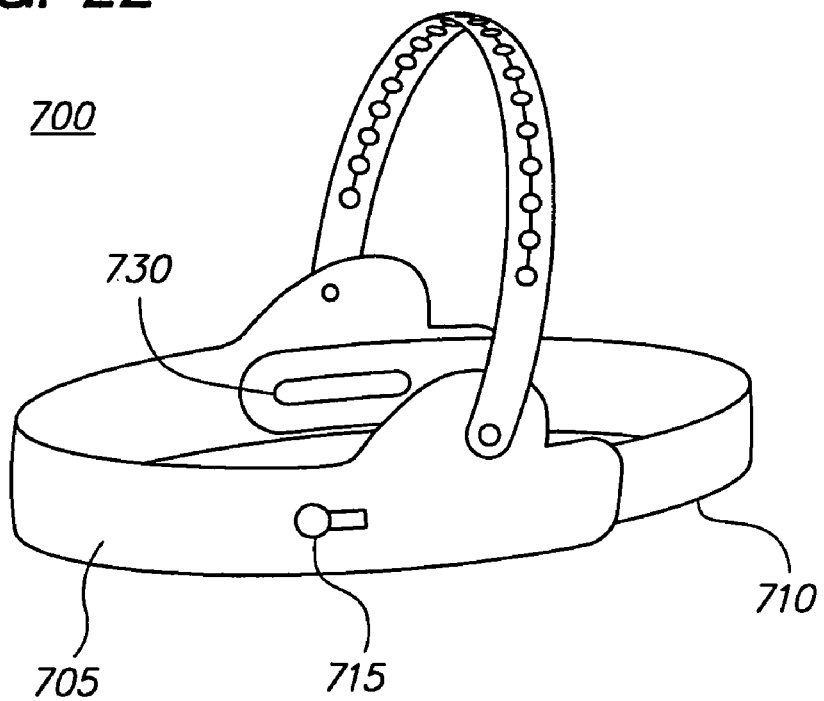
FIG. 22 is a side view of a clamp locking breast immobilization assembly that can be used in the breast tissue ablation assembly of FIG. 12.

FIG. 22 illustrates a clamp locking breast immobilizing assembly 700 constructed in accordance with a preferred embodiment of the present invention. The clamp locking breast immobilizing assembly 700 can be used in lieu of the expandable breast immobilizing assembly 505—previously described—in the breast tissue ablation system 500. The clamp locking breast immobilizing assembly 700 generally comprises a substantially rigid first member 705 on which a medical device holder 510 (identical to the one used with the inflatable breast immobilizing assembly 505) is mounted, a substantially rigid second member 710, and clamps 715 locking the first and second members 705 and 710 to each other. As shown in FIG. 22, one of the first and second members 705 and 710 comprises one or more slots 730, and the other of the first and second members 705 and 710 comprises one or more cams 745 that slide within the one or more slots 730. Moreover, in the illustrated embodiment, the members 705 and 710 are shaped so that they can be conveniently placed over and encompass the base of the breast.

Although the illustrated embodiment has the medical device holder 510 mounted on the first member 705, one of ordinary skill in the art will appreciate that the medical device holder 510 can be mounted to the second member 710 or to both the members 705 and 710. In addition, while the illustrated embodiment has two rigid members, it will be appreciated that alternate constructions can be used without departing from the spirit of the present invention. For example, more than two members can be used.

In the illustrated embodiment, the members 705 and 710 take the forms of substantially semicircular pieces, which when joined together form a substantially circular ring. However, other shapes can be used. For example, the members 705 and 710 can be constructed so that when they are joined together they form an oval or an ellipse. The members 705 and 710 are composed of a suitably rigid material, such as, for example, plastic or metal. In the preferred embodiment, the members 705 and 710 are composed of a radio-lucent material to permit monitoring of the medical treatment using, for example, a computerized axial tomography scanner (not shown) or a magnetic resonance imaging device (also not shown).

As in the discussion of the inflatable breast immobilizing assembly 505, the medical device holder 510 can pivot at the connections 740 where it is mounted, and can be locked into place at the connections 740 using a standard locking mechanism. Thus, the medical device holder 510 further comprises a locking mechanism (not shown) for locking the curved member 517 into place. In the preferred embodiment, the locking mechanism takes the form of a tightening screw. However, other types of locking mechanisms, such as a tightening clamp, can be used as well without departing from the spirit of the present invention. In addition, other designs can be used for connecting the medical device holder 510 to the first member 715. For example, the first member 715 need not have the antipodally positioned, raised brackets 735 shown in FIG. 22. Moreover, the connections 740 need not be antipodally positioned.

Figure 23:
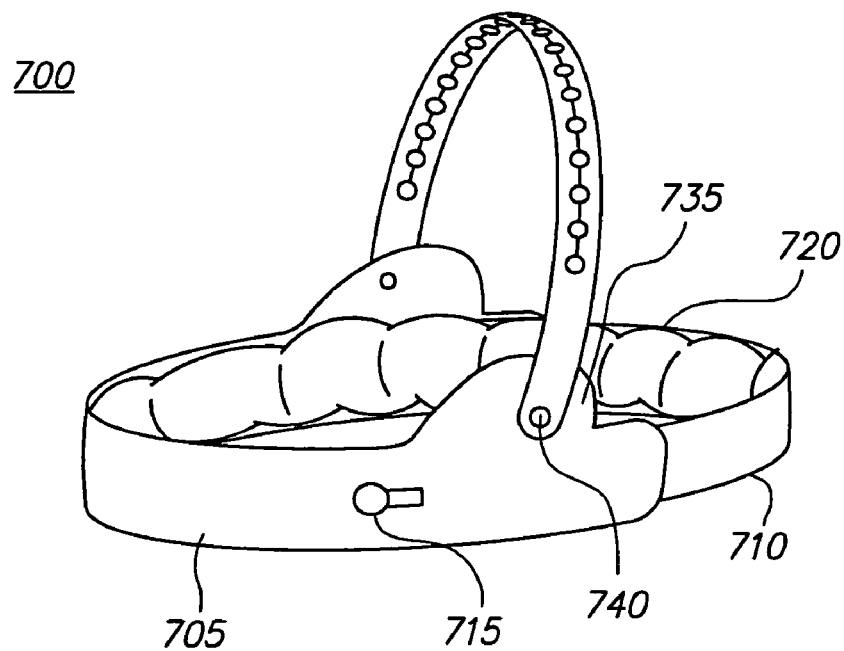
FIG. 23 is a side view of the clamp locking breast immobilization assembly of FIG. 12, wherein an optional cushioning member is particularly shown.
Figure 24:
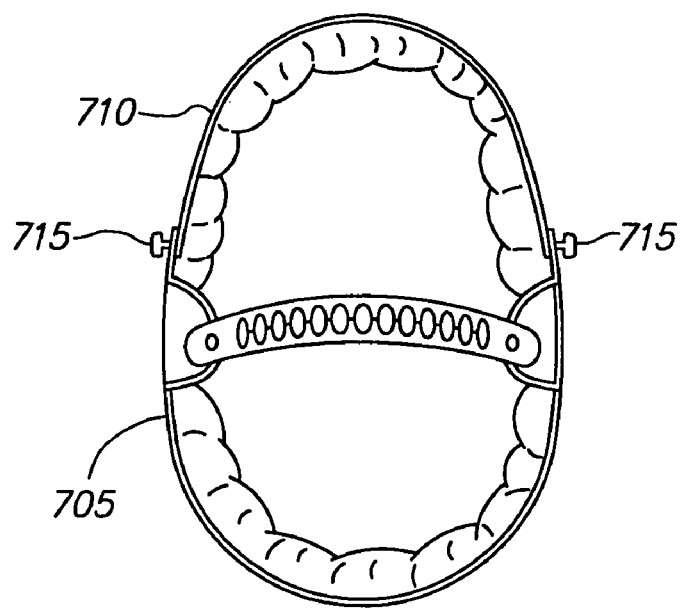
FIG. 24 is a top view of the clamp locking breast immobilization assembly of FIG. 23.

Referring to FIGS. 23 and 24, the clamp locking breast immobilizing assembly 700 is shown with an optional cushioning member 720 mounted on the inside of the first and second members 705 and 710. The cushioning member 720 can be made of any soft, compliant material that will provide cushioning for the breast. In a preferred embodiment, the cushioning member 720 is constructed of pliable plastic filled with saline solution or silicone gel, and is suitably bonded to the inside surfaces of the members 705 and 710.

Figure 25:
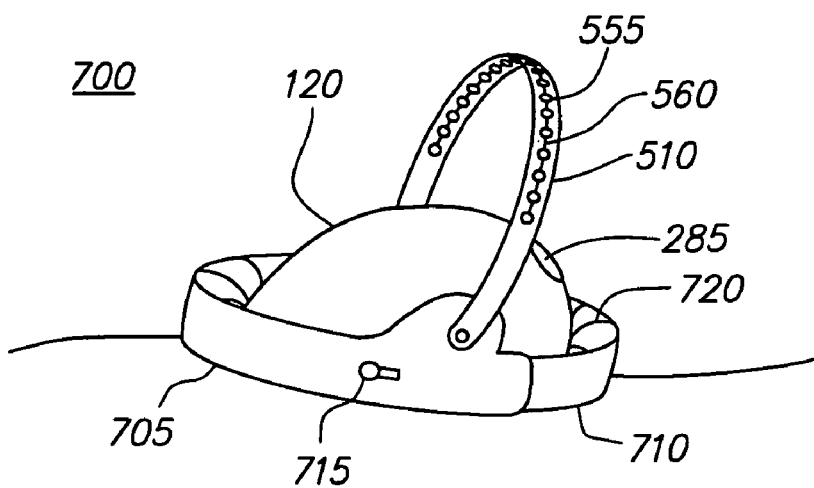
FIGS. 25-26 are views showing the operation of the breast immobilization assembly of FIG. 23 in immobilizing a breast.
Figure 26:
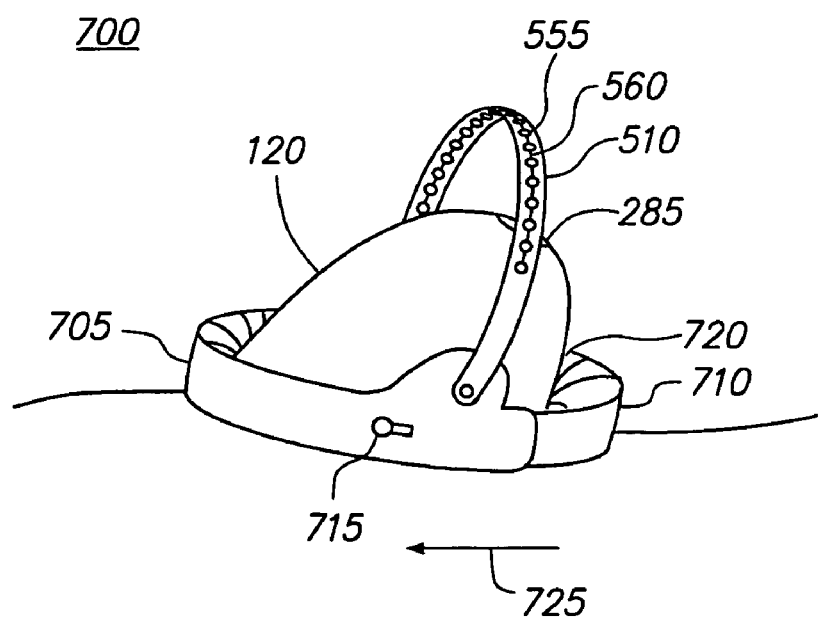

The structure and use of the clamp locking breast immobilizing assembly 700 are very similar to those of the inflatable breast immobilizing assembly 505. The difference between the two assemblies is in the ways they operate to lift the breast 120. FIGS. 25 and 26 illustrate the use of the clamp locking breast assembly 700. As shown in FIG. 25, the assembly is placed over the breast 120. Then as shown in FIG. 26, the physician moves the second member 710 in the direction 725 of the first member 705. This action causes the breast 120 to be lifted up and away from the patient's body. Once the breast 120 is sufficiently elevated, the physician locks the members 705 and 710 together using a tensioning clamp 715 or other suitable locking mechanism. The physician can then proceed as before, to perform an ablation or take a biopsy or perform some other medical treatment on the breast 120.

One benefit to this particular embodiment of a breast immobilizing assembly 700 is that it can accommodate the significant variation in breast size within the general population because its size is adjustable using the locking clamps 715. Moreover, it can be made for either a one time use—i.e., disposable—or for multiple uses. When it is made to be reused, the cushioning member 720, and the members 705 and 710 are constructed of material that can withstand standard sterilization techniques—autoclave sterilization, chemical sterilization, etc.

Although particular embodiments of the present invention have been shown and described, it should be understood that the above discussion is not intended to limit the present invention to these embodiments. Those of ordinary skill in the art will appreciate that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical system for use with a breast of a patient, comprising:
    a breast immobilizer for immobilizing and lifting the breast away from a chest wall of the patient while the patient is lying supine; and
    a medical device holder for holding a medical probe relative to the breast immobilizer, the medical device holder being movably mounted relative to the breast immobilizer to allow the medical probe to be positioned within a first angular range about the breast, the medical device holder including an elongated member comprising a channel containing a compliant membrane, the compliant membrane having a plurality of holes extending lengthwise along the compliant membrane and a slit connecting the plurality of holes, the compliant membrane further configured for slidable movement of the medical probe along the slit for selective positioning in the plurality of holes to allow the medical probe to be positioned within a second angular range about the breast.

2. The medical system of claim 1, wherein the breast immobilizer comprises a vacuum housing having a cavity for applying a vacuum to the breast.

3. The medical system of claim 2, wherein the vacuum housing comprises an access opening to expose a portion of the breast when housed within the cavity.

4. The medical system of claim 2, further comprising a vacuum conduit formed through the vacuum housing in communication with the cavity, and a relief valve in communication with the vacuum conduit.

5. The medical system of claim 1, wherein the breast immobilizer comprises a support member configured for at least partially encompassing a base of the breast to support the breast mass.

6. The medical system of claim 5, wherein the support member is a unibody support member.

7. The medical system of claim 5, wherein the support member comprises first and second members slideably affixed to each other.

8. The medical system of claim 1, wherein the medical device holder is mounted to the breast immobilizer.

9. The medical system of claim 1, wherein the medical device holder is detachably mounted to the breast immobilizer.

10. The medical system of claim 1, wherein the medical device holder comprises a locking mechanism.

11. The medical system of claim 1, wherein the breast immobilizer has structure with an inner curved surface configured to conform to at least a two hundred seventy degree region of the breast.

12. The medical system of claim 1, further comprising the medical probe.

13. The medical system of claim 1, wherein the first angular range is yaw angular range.

14. The medical system of claim 13, wherein the second angular range is an elevation angular range.

15. The medical system of claim 1, wherein the first angular range is in an elevation angular range.

16. The medical system of claim 15, wherein the second angular range is in an azimuth angular range.

17. The medical system of claim 1, wherein the elongated member includes an arm that rotates about a single point.

18. The medical system of claim 1, wherein the elongated member includes a curved member that hinges about two points.

* * * * *